United States Patent [19]

Fried

[11] Patent Number: 5,162,579
[45] Date of Patent: Nov. 10, 1992

[54] PREPARATION OF ALKOXYALKANOIC ACIDS

[75] Inventor: Herbert E. Fried, Houston, Tex.
[73] Assignee: Shell Oil Company, Houston, Tex.
[21] Appl. No.: 752,386
[22] Filed: Aug. 30, 1991
[51] Int. Cl.$^5$ .................. C07C 51/16; C07C 51/235; C07C 51/245; C07C 51/27
[52] U.S. Cl. .................... 562/537; 562/538; 562/540; 562/587
[58] Field of Search ............... 562/538, 537, 587, 540

[56] References Cited

U.S. PATENT DOCUMENTS 4,620,033 10/1986 Isshiki et al. .................. 562/519

FOREIGN PATENT DOCUMENTS 5096516 11/1986 Japan .

OTHER PUBLICATIONS

Miyazawa et al., "Oxidation of Benzyl Alcohol with Iron(III) Using Polymers Containing Nitroxyl Radical Structure as a Mediator," J. Polym. Sci., Polym. Chem. Ed., 23(9), 1985, pp. 2487–2494.
Grigor'ev et al., "Participation of Nitroxyl Radical in the Oxidation of Aldehyde and Alcohol Groups in 3-imidazolin-1-oxyls," Izc. AKad. Nauk SSSR, Ser. Khim., (1), 1978, pp. 208–210.
Miyazawa et al., "Oxidation of Benzyl Alcohol with Copper(II) Mediated by a Polymeric Oxoaminium Salt," J. Mol. Catal., 49(1), 1988, 131–134.
Ganem et al., "Biological Spin Labels as Organic Reagents. Oxidation of Alcohols to Carbonyl Compounds Using Nitroxyls," J. Org. Chem., 40(13), 1975, pp. 1998–2000.
Miyazawa et al., "Oxidation of Benzyl Alcohol by Iron(III) Mediated by Nitroxyl Radical," J. Mol. Catal., 31(2), 1985, pp. 217–220.
Anelli et al., "Fast and Selective Oxidation of Primary Alcohols to Aldehydes or to Carboxylic Acids and of Secondary Alcohols to Ketones Mediated by Oxoammonium Salts under Two-Phase Conditions," J. Org. Chem., 52 (12), pp. 2559–2562 (1987).
Inokuchi et al., "A Selective and Efficient Method for Alcohol Oxidations Mediated by N-Oxoammonium Salts in Combination with Sodium Bromite," J. Org. Chem., 1990, 55, pp. 462–466.
Organic Synthesis, vol. 69, p. 212 (1990).
Semmelhack et al., "Oxidation of Alcohols to Aldehydes and Oxygen and Cupric Ion, Mediated by Nitrosonium Ion," J. Am. Chem. Soc. 1984, 106, 3374–3376.
Yamaguchi et al., "Application of Redox System Based on Nitroxides to Organic Synthesis," Pure & Applied Chemistry, vol. 62(2), 1990, pp. 217–222.

Primary Examiner—José G. Dees
Assistant Examiner—Joseph M. Conrad
Attorney, Agent, or Firm—Pamela J. McCollough

[57] ABSTRACT

A process for the preparation of an alkoxyalkanoic acid of the formula $$RO(CH_2CHR'O)_nCH_2CO_2H$$

wherein R is an alkyl group of from 1 to about 22 carbon atoms, R' is hydrogen or methyl or mixtures thereof (on the individual molecule) and n is an integer of from 1 to about 12, which comprises reacting the corresponding alkoxyalkanol with a stable free radical nitroxide having the formula:

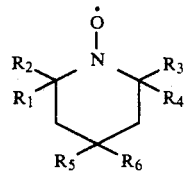

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, and nitric acid in the presence of an oxidant at a temperature in the range of from about 0° C. to about 100° C. and thereafter separating out the alkoxyalkanoic acid.

15 Claims, No Drawings

PREPARATION OF ALKOXYALKANOIC ACIDS

FIELD OF THE INVENTION

This invention relates to a process for the preparation of alkoxyalkanoic acids by the oxidation of the corresponding alkoxyalkanols in the presence of a stable free radical nitroxide, nitric acid and an oxidant.

BACKGROUND OF THE INVENTION

Alkoxyalkanoic acids are useful as anionic detergents. These acids, being composed of only the elements C, H and O, do not pose the environmental problems that other detergents containing heteroatoms such as N, S, and P pose. Commercially, the alkoxyalkanoic acids are prepared in a two-step process of first reacting an alkoxyalkanol with sodium and then reacting the resultant alkoxide with the sodium salt of chloroacetic acid.

It is also known to convert alkoxyalkanols such as methyl carbitol to the corresponding carboxylic acids by oxidizing them with nitric acid. However, not all of the nitric acid can be separated by distillation, and the reaction product contains nitric acid, which is corrosive and therefore undesirable. In addition, cleavage of the ether linkages occurs to a large degree during this process.

Japanese Patent No. 50-96516, issued Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.–270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, vol. 52 (12), pp. 2559–2562; *Pure and Applied Chemistry*, vol. 62(2), 1990, pp. 217–222; *Journal of Organic Chemistry*, vol. 55, 1990, pp. 462–466. The primary products produced in these processes are aldehydes and the stoichiometrically consumed oxidant is hypochlorite.

It is generally more difficult to oxidize alkoxyalkanols than alkanols as it is difficult to oxidize alkoxyalkanols without splitting the molecular chain at the ether linkage and thereby produce a large proportion of undesired by-product.

OBJECTS OF THE INVENTION

It is therefore an object of this invention to produce alkoxyalkanoic acids in high yields and with high selectivities from alkoxyalkanols without producing large amounts of other products such as aldehydes and esters.

It is a further object of this invention to provide a process for the preparation of alkoxyalkanoic acids in which highly corrosive, difficult to separate, side-products are not formed.

It has been found that alkoxyalkanoic acids can be produced in high yields and with high selectivities by using catalytic amounts of a stable free radical nitroxide, nitric acid and an oxidant.

SUMMARY OF THE INVENTION

This invention relates to a process for the preparation of an alkoxyalkanoic acid of the formula $$RO(CH_2CHR'O)_nCH_2CO_2H$$

wherein R is an alkyl group of from 1 to about 22 carbon atoms, R' is hydrogen or methyl or mixtures thereof (on the individual molecule) and n is an integer of from 1 to about 12 which comprises reacting the corresponding alkoxyalkanol with a stable free radical nitroxide having the formula:

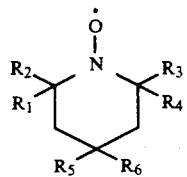

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, and nitric acid in the presence of an oxidant at a temperature in the range of from about 0° C. to about 100° C. and thereafter separating out the alkoxyalkanoic acid.

DESCRIPTION OF THE PREFERRED EMBODIMENTS

The present process converts alkoxyalkanols of the formula $$RO(CH_2CHR'O)_nCH_2CH_2OH \qquad (I)$$

wherein R is an alkyl group, preferably 1 to about 22; more preferably about 11 to about 18 carbon atoms, R' is hydrogen or methyl or mixtures thereof (on the individual molecule) and n represents the average number of oxyalkylene groups and is an integer of from 1 to about 12, preferably of from about 2 to about 9, to the corresponding alkoxyalkanoic acids of the formula:

$$RO(CH_2CHR'O)_nCH_2CO_2H \qquad (II)$$

by contacting the alkoxyalkanol with a stable free radical nitroxide and nitric acid in the presence of an oxidant at a temperature in the range of from about 0° C. to about 100° C. and thereafter separating out the alkoxyalkanoic acid. The R group in the above formula I can be substituted with any substituent which does not interfere with the oxidation of the hydroxy group. Such substituents include —OR", —CH₃, —COOH, CONH₂ and COOR" wherein R" is an alkyl or aryl group. The process of the instant invention is particularly suited to detergent range ethoxylated, or propoxylated alcohols with alkyl chains (R) of about 8 to about 20, preferably of about 11 to about 18 carbon atoms. The R' groups on an individual molecule can be hydrogen, methyl or mixtures thereof. For example, straight ethoxylated, straight propoxylated and mixed ethoxylated-propoxylated detergent alcohols are comercially available. The number of such alkoxylate groups, (CH₂CHR'O), range from 1 to about 20. Commercially, detergent range ethoxylate alcohols are available with an average of 3, 7, 9 and 12 ethoxylate units per molecule. Others can be readily prepared. In a preferred embodiment, the starting alkoxyalkanol is ethoxylated alcohol which has had the unreacted alcohols and lower ethoethoxylates topped off in order to give an ethoxylate having about four ethylene oxide units per molecule.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the presursor to a stable free radical from which the stable free radical may be produced in situ.

The stable free radical nitroxides, as used in the present process, are precursors to catalysts, i.e., oxoammonium salts, active for the oxidation of alkanols to the corresponding acids. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

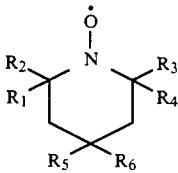

wherein each of $R_1$, $R_2$, $R_3$ and $R_4$ is an alkyl, aryl or heteroatom substituted alkyl group having 1 to about 15 carbon atoms and no hydrogen is bound to the remaining valences on the carbon atoms bound to the nitrogen, and each of $R_5$ and $R_6$ is alkyl, hydrogen, aryl or a substituted heteroatom. As used herein, the term "alkyl" is meant to include cycloalkyl. The alkyl (or heteroatom substituted) groups $R_1$-$R_4$ may be the same or different, and preferably contain 1 to 15 carbon atoms. Preferably, $R_1$-$R_4$ are methyl, ethyl, or propyl groups. In addition to hydrogen, the heteroatom substituents may include, halogen, oxygen, nitrogen and the like. Preferably, one of $R_5$ and $R_6$ is hydrogen, with the other one being a substituted heteroatom which does not interfere with the reaction. Suitable substituted heteroatoms include

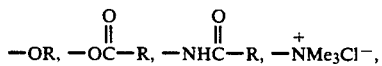

$-O-SO_3H$, $-O-$polymer and the like.

In a preferred embodiment, the nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl, and mixtures thereof, with 2,2,6,6-tetramethyl-piperidine-1-oxyl, 2,2,6,6-tetramethyl-piperidine-1-oxyl-4-sulfate, and 4-alkoxy-2,2,6,6-tetramethyl-piperidine-1-oxyl being particularly preferred.

As used herein, the term "nitric acid" refers to nitric acid, fuming nitric acid or nitrous acid generated by contacting alkali metal nitrate with mineral acid. The nitric acid suitable for use in the present invention typically has a concentration in the range of from about 50 percent to about 100 percent, preferably about 70 percent. Generally, an amount of nitric acid in the range of from about 5 mole percent to about 100 mole percent, basis the moles of starting alkoxyalkanol is utilized. If excess nitric acid is used and the reaction mixture becomes too acidic, the reaction stops. The nitric acid is typically added to the reaction mixture after all of the other reactants have been added. While not wishing to be bound by any particular theory, it is believed that nitrogen oxides ($NO_X$) are generated in the reaction and are the active species in the reaction.

The oxidants suitable for use in the instant invention are those compounds which are capable, in the presence of nitric acid, of oxidizing the stable free radical nitroxide to the oxoammonium salt. Suitable oxidants include oxygen-containing gases such as pure oxygen and oxygen in air. Whereas pure oxygen can is preferred to accomplish the desired conversion, the oxygen can also be diluted with an inert gas such as nitrogen, helium, argon, or other similar gas. While air can be used as the oxidant, the reaction rate is much slower. For purposes of increasing the reaction rate, higher $O_2$ pressures such as, for example, 1000 psi can be utilized. In a preferred embodiment, pure oxygen is used as the oxidant and it is bubbled into the reaction solution. In another embodiment, air can be bubbled initially through the reaction solution in order to commence the reaction.

The amounts and concentrations of the reactants utilized in the process of the instant invention can vary within wide ranges. The amount of stable free radical nitroxide is typically in the range of from about 1 mole percent to about 50 mole percent, preferably from about 5 mole percent to about 20 mole percent, basis the number of moles starting alkoxyalkanol. Generally, the amount of nitric acid used is in the range of from about 5 mole percent to about 100 mole percent, basis the number of moles of alkoxyalkanol.

The process of the present invention is typically conducted under mild conditions, with good results being obtained using a temperature in the range of from about 0° C. to about 100° C., preferably about 20° C. to about 70° C., and most preferably, about 40° C. to about 60° C. Reaction pressures are not critical although higher pressures result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.032 moles of alkoxyalkanol, and 0.006 moles percent by weight of the nitroxide, may be added to the reaction vessel, followed by the addition of 0.016 moles of 70 percent nitric acid and bubbling $O_2$ through the reaction mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. Phase separation of the final product mixture takes place at 100° C. with water. The reaction product can be purified by a number of conventional means such as high temperature water washing or catalytic hydrogenation.

Depending upon process conditions and the nitroxide used, the yields of alkoxyalkanoic acid obtained by this invention can be greater than about 98% of starting material being converted. The products produced by the instant process can be used in a variety of detergent applications. For example, light duty dishwashing liquids, shampoos and heavy duty laundry liquids or powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

In the following examples, the starting alkoxyalkanol was a NEODOL ® Ethoxylate 23-3T alcohol which was prepared by ethoxylating a mixture of $C_{12}$ and $C_{13}$ substantially straight chain alcohols ($C_{12}$:$C_{13}$~40:60) to an ethoxylate alcohol having about 3 ethylene oxide units per molecule and then topping off the unreacted alcohols and lower ethoxylates so that the final product has about three ethylene oxide units per molecule.

EXAMPLE 1

Twelve grams of NEODOL ® Ethoxylate 23-3T, 0.3 grams of 2,2,6,6-tetramethyl-piperidine-1-oxyl, and 1 gram of 70 percent nitric acid were charged to a 50 milliliter round bottomed flask. To this mixture was added $O_2$. The reaction temperature was held at 40° C. over a 3-hour period. The results are presented in Table I.

EXAMPLE 2

Twelve grams of NEODOL ® Ethoxylate 23-3T, 1 gram of 2,2,6,6-tetramethyl-piperidine-1-oxyl, and 1 gram of 70 percent nitric acid were charged to a 50 milliliter round bottomed flask. To this mixture was added $O_2$. The reaction was held at ambient temperature over a 6-hour period. The results are presented in Table I.

EXAMPLE 3

Twelve grams of NEODOL ® Ethoxylate 23-3T, 0.3 grams of 2,2,6,6-tetramethyl-piperidine-1-oxyl, and 1 gram of 70 percent nitric acid were charged to a 50 milliliter round bottomed flask. To this mixture was added $O_2$. The reaction temperature was held at room temperature over a 6-hour period. The results are presented in Table I.

COMPARATIVE EXAMPLE A

Comparative Example A was carried out in a manner similar to Example 2 except that no nitroxide was used and the reaction was allowed to run for 16 hours. The results are presented in Table I.

COMPARATIVE EXAMPLE B

Comparative Example B was carried out in a manner similar to Example 2 except that no nitric acid was used and the reaction was allowed to run for 16 hours. The results are presented in Table I.

COMPARATIVE EXAMPLE C

Comparative Example C was carried out in a manner similar to Example 2 except that 50 milliliters of teritary butyl alcohol was added and the reaction was carried out over a period of 16 hours. The results are presented in Table I.

As can be seen in Table I, nitroxide and nitric acid are necessary for the oxidation of the alkoxyalkanol to proceed. Comparative Example C illustrates the deleterious effect of solvent.

TABLE I

Oxidation Of Alkoxyalkanols to Alkoxyalkanoic Acids

|  | % Conversion | % Sel. Acids | % Sel. Esters + Heavies | % Sel. Aldehydes |
|---|---|---|---|---|
| Example 1 | >99.5 | 98 | 1.5 | <1 |
| Example 2 | >99.5 | 91 | 7 | <2 |
| Example 3 | 98.5 | 86 | 8 | 6 |
| Comparative Example A | 0 | 0 | 0 | 0 |
| Comparative Example B | 0 | 0 | 0 | 0 |
| Comparative Example C | 16 | 0 | 0 | 100 |

What is claimed is:

1. A process for the preparation of an alkoxyalkanoic acid of the formula $$RO(CH_2CHR'O)_nCH_2CO_2H$$

wherein R is an alkyl group of from 1 to about 22 carbon atoms, R' is hydrogen or methyl or mixtures thereof (on the individual molecule) and n is an integer of from 1 to about 12, which comprises reacting the corresponding alkoxyalkanol with a stable free radical nitroxide having the formula:

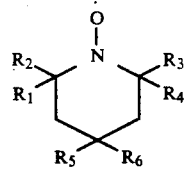

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, and nitric acid in the presence of an oxidant at a temperature in the range of from about 0° C. to about 100° C. and thereafter separating out the alkoxyalkanoic acid.

2. The process of claim 1 wherein the stable free radical nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-oxo-2,2,6,6-tetramethyl-piperidine, 4-alkoxy-2,2,6,6-tetramethyl-piperidine and mixtures thereof.

3. The process of claim 2 wherein the stable free radical nitroxide is selected from the group consisting of 2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

4. The process of claim 1 wherein said nitric acid has a concentration in the range of from about 50 percent to about 100 percent.

5. The process of claim 4 wherein said nitric acid has a concentration of about 70 percent.

6. The process of claim 1 wherein the amount of nitric acid is in the range of from about 5 mole percent to about 100 mole percent, basis the number of moles alkoxyalkanol.

7. The process of claim 1 wherein said alkoxyalkanol is contacted with said stable free radical nitroxide, followed by the addition thereto of said nitric acid and said oxidant.

8. The process of claim 7 wherein the amount of stable free radical nitroxide is in the range of from about 1 mole percent to about 50 mole percent, basis the number of moles of alkoxyalkanol.

9. The process of claim 8 wherein the amount of stable free radical nitroxide is in the range of from about 5 mole percent to about 20 mole percent, basis the number of moles of alkoxyalkanol.

10. The process of claim 7 wherein the amount of nitric acid is in the range of from about 5 mole percent to about 100 mole percent, basis the number of moles of alkoxyalkanol.

11. The process of claim 1 wherein said oxidant is an oxygen-containing gas.

12. The process of claim 11 wherein said oxygen containing gas is selected from the group consisting of pure oxygen and air.

13. The process of claim 12 wherein said oxygen-containing gas is pure oxygen.

14. The process of claim 1 wherein said process is carried out at a temperature in the range of from about 20° C. to about 70° C. and at atmospheric pressure.

15. The process of claim 14 wherein said process is carried out at a temperature in the range of from about 40° C. to about 60° C. and at atmospheric pressure.

* * * * *